United States Patent
Lönnerdal et al.

(10) Patent No.: US 9,889,162 B2
(45) Date of Patent: Feb. 13, 2018

(54) PROPHYLACTIC USE FOR PREVENTION OF INFECTIONS

(71) Applicant: HERO AG, Lenzburg (CH)

(72) Inventors: Bo Lönnerdal, Davis, CA (US); Olle Hernell, Umeå (SE); Lars-Börje Sjöberg, Vallentuna (SE); Catharina Tennefors, Enebyberg (SE)

(73) Assignee: HERO AG, Lenzburg (CH)

( * ) Notice: Subject to any disclaimer, the term of this patent is extended or adjusted under 35 U.S.C. 154(b) by 146 days.

(21) Appl. No.: 14/902,123

(22) PCT Filed: Jun. 26, 2014

(86) PCT No.: PCT/EP2014/063538
§ 371 (c)(1),
(2) Date: Dec. 30, 2015

(87) PCT Pub. No.: WO2015/000788
PCT Pub. Date: Jan. 8, 2015

(65) Prior Publication Data
US 2016/0158287 A1   Jun. 9, 2016

(30) Foreign Application Priority Data
Jul. 1, 2013 (SE) .................................... 1350804

(51) Int. Cl.
| | | |
|---|---|---|
| A61K 36/00 | (2006.01) | |
| A61K 35/20 | (2006.01) | |
| A61K 38/01 | (2006.01) | |
| A61K 38/02 | (2006.01) | |
| A23L 33/00 | (2016.01) | |
| A23L 33/115 | (2016.01) | |
| A23L 33/19 | (2016.01) | |

(52) U.S. Cl.
CPC ............ *A61K 35/20* (2013.01); *A23L 33/115* (2016.08); *A23L 33/19* (2016.08); *A23L 33/40* (2016.08); *A61K 38/018* (2013.01); *A61K 38/02* (2013.01); *A23V 2002/00* (2013.01)

(58) Field of Classification Search
CPC ..................................................... A61K 35/20
See application file for complete search history.

(56) References Cited

U.S. PATENT DOCUMENTS

2008/0003330 A1   1/2008   Rueda et al.

FOREIGN PATENT DOCUMENTS

| EP | 2047856 A1 | 4/2009 |
|---|---|---|
| FR | 2908605 A1 | 5/2008 |
| FR | 2930406 A1 | 10/2009 |
| WO | WO-2007/073192 A2 | 6/2007 |
| WO | WO-2009/020405 A1 | 2/2009 |
| WO | WO-2011/069987 A1 | 6/2011 |
| WO | WO-2012/170021 A1 | 12/2012 |
| WO | WO-2013/153071 A2 | 10/2013 |

OTHER PUBLICATIONS

Bezelgues et al, Milk fat globule membrane as a potential delivery system for liposoluble nutrients. Journal of Dairy Science (2009), 92(6), 2524-2528.*
Jerry A. Peterson et al., "Structural and Functional Aspects of Three Major Glycoproteins of the Human Milk Fat Globule Membrane," Advances in Experimental Medicine and Biology, Springer, US, XP009052067, Jan. 1, 2001, pp. 179-187, vol. 501.
Ricardo Rueda, "The role of dietary gangliosides on immunity and the prevention of infection," British Journal of Nutrition, XP-002729764, 2007, pp. S68-S73, vol. 98, No. 1.

* cited by examiner

*Primary Examiner* — Qiuwen Mi
(74) *Attorney, Agent, or Firm* — Drinker Biddle & Reath LLP

(57) ABSTRACT

The present invention concerns the field of nutritional compositions and concerns a nutritional composition, especially an infant formula containing whey protein/milk protein concentrate solids rich in phospholipids, rich in MFGM for use in the prophylaxis and prevention of infectious morbidity, especially otitis. At the same time the use of antipyretics has diminished.

17 Claims, 1 Drawing Sheet

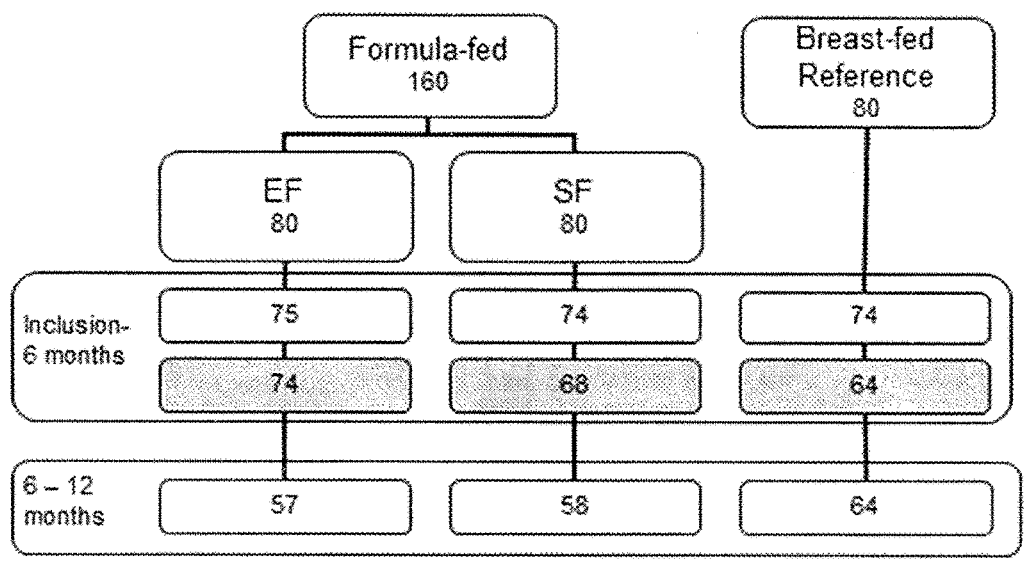

PROPHYLACTIC USE FOR PREVENTION OF INFECTIONS

CROSS-REFERENCE TO PRIOR APPLICATION

This application is a §371 National Stage Application of PCT International Application No. PCT/EP2014/063538 filed Jun. 26, 2014, which claims priority to Swedish Application No. 1350804-9 filed Jul. 1, 2013, the entire contents of each is incorporated herein by reference.

FIELD OF INVENTION

The present invention concerns a new use of nutritional compositions for infants for example infant formulas.

BACKGROUND

There are differences seen in morbidity between breastfed and formula-fed infants. Breastfed infants have less respiratory infections, ear infections and gastroenteritis than formula-fed infants. (A. L. Wright et al. *BMJ*, vol. 299, 946-949, B. Duncan et al. *Pediatrics*, 2003, vol. 91 (5) 867-873, G. Aniansson et al. *Pediatr Infect Dis J*, 1994, vol. 13 (3) 182-188 and K. G. Dewey et al. *J Pediatr*, 1992, vol 126 (No. 5) part 1 695-702). One possible explanation is that breast milk contains more immune modulating substances than cow's milk.

Sialic acid is found in milk both bound to proteins, e.g. kappa-casein with its content of glyco macro peptide (cGMP), and lipid bound in gangliosides. Sialic acid is found in high concentrations in human brain and breast milk and has been proposed as a milk factor that could have an impact on the development of the central nervous system (B. Wang et al. *Eur J Clin Nutr*, (2003) 57, 1351-1369). Enrichment of sialic acid in the diet of piglets has been shown to improve memory and learning (B. Wang et al. *Am J Clin Nutr*, 2007; 85:561-569).

Furthermore, long-chain polyunsaturated fatty acids (LCPUFA) have a clear impact on the developing nervous system. Breastfed children have higher levels of arachidonic acid (ARA) and docosahexaenoic acid (DHA) in both blood and brain than children who received formula without the addition of ARA and DHA (M. Makrides et al. *Am J, Clin Nutr* 1994; 60:189-94).

Dietary sphingomyelin is probably also important for the development of an infant's nervous system. In studies with rat it is shown that enrichment with sphingomyelin in the diet increases the myelisation of the nervous system (K. S. T. Oshida et al. *Pediatr Res*, 2003. 53: p. 589-593). Breast milk contains sphingomyelin and the amount is between 5-13 mg/100 ml.

(García et al *Food Chem* 2012 135(3): p 1777-1783) *Phospholipid fingerprints of milk from different mammalians determined by* 31 *NMR*)

SPECIAL BACKGROUND

Another document describing that breast-feeding is protective against otitis, lower respiratory tract infections and gastrointestinal infections is (Ip, S., et al., *A summary of the Agency for Healthcare Research and Quality's evidence report on breastfeeding in developed countries*. Breastfeed Med, 2009. 4 Suppl 1: p. S17-30). Also commentary by the ESPGHAN Committee (JPGN, 2009, 49: p 112-125). This is probably due to antimicrobial factors in human milk including growth promoters of protective enteric bacteria agents, enzymes that lyse bacteria, antibodies, oligosaccharides, glycosylated proteins, antiviral lipids and leukocytes (Labbok, M. H., D. Clark, and A. S. Goldman, *Breastfeeding: maintaining an irreplaceable immunological resource*. Nat Rev Immunol, 2004. 4(7): p. 565-72.2). During the last decades, the milk fat globule membrane (MFGM), a small but biologically active milk fraction, has gained interest of having health promoting effects in several areas, including infections (Spitsberg, V. L., *Invited review: Bovine milk fat globule membrane as a potential nutraceutical*. J Dairy Sci, 2005. 88(7): p. 2289-94.3). The MFGM fraction has historically been discarded in the manufacturing of infant formula. Recently, bovine MFGM-enriched milk fractions have become commercially available, but, to our knowledge, MFGM supplementation to infant formula for prophylaxis and prevention of infections, especially otitis has never been studied before. MFGM comprises 120 different proteins in a phospholipidic double layer which surrounds fat droplets within the milk.

PRIOR ART

None of the prior art discloses a nutritional composition for infants that can be used for phrophylaxis and prevention of infections, especially otitis and thus reduce the use of antipyretics.

OBJECT OF THE INVENTION

The present study is part of a randomized controlled trial with the overall aim to evaluate health effects on infants fed an experimental formula (EF) with reduced energy and protein content and with supplementation with a bovine MFGM fraction. Primary outcomes in the main trial were weight at 6 months, body composition at 4 months and cognitive function at 12 months. As described by the present inventors in WO2013/153071, the EF group up-regulated their ingested volumes during the intervention, hence the total energy and protein intake was similar in both groups during intervention, and linear and ponderal growth and body composition was similar until 6 months. The object that now has been evaluated was to elucidate whether the EF, compared to the standard formula (SF), can influence the risk of infectious diseases and other disease symptoms in formula-fed infants in a favorable way to levels more close to breast-fed infants. The hypothesis was that infants receiving the EF formula would have fewer infections during the first 12 months compared to infants receiving the SF formula, and at a level more similar to breast-fed infants.

SUMMARY OF THE INVENTION

Use of the nutritional composition during the first 6 months of life of an infant as the only nutrition, or from birth to up to 12 months of age as a complementary diet may for example minimize the difference in growth and/or body composition (weight (wt) % fat) and/or cholesterol levels and/or blood urea nitrogen values and/or plasma amino acids and/or sialic acid in saliva and/or fasting insulin levels and/or cognitive function and/or occurrence of obesity in childhood between breastfed and formula-fed children. It has now also been identified that morbidity and/or infection parameters between breastfed and formula fed children given the new nutritional formulation (EF) has changed in a positive way and the new nutritional formulation (EF) containing MFGM in a whey protein/milk protein concentrate solids rich in phospholipids containing bioactive compounds, such as lactoferrin, α-lactalbumin, butyrophilin, MUC1, PAS6/7 (lactadherin), gangliosides, CD14, TLR1 and TLR4, IgG, cGMP, sialic acid and phospholipids (for example sphingomyelin, phosphatidyl choline, phosphatidyl serine and phosphatidyl ethanolamine) is effective for prevention and as prophylaxis for infections especially otitis.

Whey Protein Concentrates Solids (Rich in Phospholipids)

Whey protein concentrate solids rich in phospholipids used as a component in the nutritional composition according to the invention is a whey protein concentrate with a high concentration of bioactive proteins and lipids. The whey protein concentrate has a high nutritional value, and is applicable in infant and clinical nutrition. Whey protein/milk protein concentrate solids rich in phospholipids contain most of the insoluble membrane protein fragments from MFGM originally present in the whey, in addition to residual whey components, proteins, lactose and salts. The invention utilizes, whey protein concentrate solids rich in phospholipids obtained after removal of the major whey proteins by known industrial processing, such as filtration, ion-exchange chromatography, and the like. This fraction contains most of the insoluble membrane fragments, which contain protein and associated fat. Similar raw materials from different suppliers may be used as enriched phospholipid whey protein/milk protein concentrate solids in a formula according to the invention.

The source of enriched phospholipid whey protein concentrate solids comprises at least 20 wt % phospholipids based on total lipid content, for example 20 to 70 wt % or for example 25 to 55 wt % phospholipids based on total lipid of the enriched phospholipid whey protein concentrate solid source.

The whey protein concentrate solids rich in phospholipids used in the nutritional composition according to the present invention is not depleted of cGMP.

The components of the whey protein concentrate solids rich in phospholipids may affect the development of the nervous system, morbidity and psychomotor development in a positive manner for infants fed with the nutritional composition according to the invention compared to infants fed standard infant formula or the control formula according to the invention.

Phospholipids are important constituents of cellular membranes contributing significantly to the membrane structure and function.

From the results in this study it can be expected that the component whey protein/milk protein solids rich in phospholipids and MFGM added to a standard formulation also would be active for prevention and prophylaxis of infections, especially otitis in children during the first six months of life.

Lacprodan MFGM-10 (from Arla foods) or similar raw materials from other suppliers may be used as enriched phospholipid whey protein concentrate solids in a formula according to the invention. For example the source of enriched phospholipid whey protein concentrate solids comprises at least 20 wt % phospholipids based on total lipid content, for example 20 to 70 wt % or for example 25 to 55 wt % phospholipids based on total lipid of the enriched phospholipid whey protein concentrate solid source.

Whey protein concentrate solids rich in phospholipids are administered either as a milk fat membrane MFGM or as the different ingredients defined above one by one, but mixed together.

It is important that the content of phospholipids based on the total lipid content comprises at least wt 20% phospholipids based on total lipid content.

The formula described in the recently filed not yet publically available PCT/EP2013/057405 may be used for the prophylaxis of infections especially otitis. No one has previously produced a formula with both low protein and low energy content, which in combination with this has high sialic acid content and high content of milk derived cholesterol with the additional characteristic that it has a prophylactic effect on infections, especially otitis.

There is nothing in the literature that would instruct the person skilled in the art to use a similar formula in such a way. Since there are many different parameters which have to be considered it was not obvious how to compose the infant formula which fulfills the need of the infants as well as the commission directive, national legislations and recommendations within the paediatric nutritional field. It was then further unexpected that the formulation also had a prophylactic effect against infections, especially otitis.

Below Different Embodiments to be Used for Prophylaxis of Infections, Especially Otitis are Shown. The Embodiments are Exemplifying Embodiments and not Limiting the Scope of the Invention Also nutritional infant formula on the market will benefit from the addition of whey protein concentrate solids rich in phospholipids and in MFGM as defined above and give a prophylactic or preventive effect.

In one embodiment of the invention the nutritional composition used according to the invention comprises;
- a total energy content of 67 kcal/100 ml or lower, for example 62 kcal/100 ml or lower, especially lower than 60 kcal/100 ml or between 58-62 kcal/100 ml or for example 58-60 kcal/100 ml
- a protein content of 1.25 g/100 ml or lower, or for example lower than 1.25 g/100 ml or for example between 1.1-1.25 g/100 ml or between 1.1 g/100 ml to lower than 1.25 g/100 ml
- whey protein/milk protein concentrate solids rich in phospholipids and MFGM containing 5-7 weight % of the total dry weight of the composition In one embodiment of the invention the nutritional composition used according to the invention comprises
- a total energy content of 67 kcal/100 ml or lower
- a protein content which is 1.5 g/100 ml or lower,
- an energy content from protein of 7.2-8.6 percentage of the total energy content of the nutritional composition,
- an energy content from fat which is at least 47 percentage or more of the total energy content of the nutritional composition,
- a medium chain fatty acid content comprising 8 to 10 carbons which is less than 3 weight % of total amount of fatty acids,
- a sialic acid content of 10-25 mg/100 ml or higher,
- a cholesterol content of 4-10 mg/100 ml
- a sphingomyelin content of 7-15 mg/100 ml In one embodiment of the invention the nutritional composition used according to the invention has a total energy content of 62 kcal/100 ml or lower and the composition comprises;
- a protein content which is 1.25 g/100 ml or lower,
- a cholesterol content of 5-10 mg/100 ml.
- whey protein concentrate solids rich in phospholipids and MFGM containing 5-7 weight % of the total dry weight of the composition In one embodiment for use according to the invention the total energy content of the nutritional composition is 67 kcal/100 ml or lower and the composition comprises;
- a protein content which is 1.5 g/100 ml or lower,
- an energy content from protein of 7.2-8.6 percent of the total energy content of the nutritional composition,
- an energy content from fat which is at least 47 percent or more of the total energy content of the nutritional composition,
- a medium chain fatty acid content comprising 8 to 10 carbons which is less than 3 weight % of total amount of fatty acids,
- a sialic acid content of 10-25 mg/100 ml or higher,
- a cholesterol content of 4-10 mg/100 ml
- a sphingomyelin content of 7-15 mg/100 ml
- whey protein/milk protein concentrate solids rich in phospholipids and MFGM in 5-7 weight % of the total dry weight of said nutritional composition.

In one embodiment the nutritional composition used according to the invention has a total energy content of 62 kcal/100 ml or lower and the composition comprises;
- a protein content which is 1.25 g/100 ml or lower,
- an energy content from protein of 7.8-8.4 percent of the total energy content of the nutritional composition,
- an energy content from fat which is at least 49 percent or more of the total energy content of the nutritional composition,
- a medium chain fatty acid comprising 8 to 10 carbons content which is less than 3 weight % of total amount of fatty acids,
- a sialic acid content of 10-25 mg/100 ml or higher,
- a cholesterol content of 5-10 mg/100 ml
- a sphingomyelin content of 9-15 mg/100 ml or higher
- whey protein/milk protein concentrate solids rich in phospholipids and MFGM containing 5-7 weight % of the total dry weight of the composition In another embodiment of the invention the nutritional composition to be used according to the invention comprises;
- a total energy content of 62 kcal/100 ml or lower, or for example lower than 60 kcal/100 ml or between 58-62 kcal/100 ml or for example 58-60 kcal/100 ml
- a protein content of 1.25 g/100 ml or lower, or for example lower than 1.25 g/100 ml or for example between 1.1-1.25 g/100 ml or between 1.1 g/100 ml to lower than 1.25 g/100 ml.
- an energy content from protein of 7.8-8.4 percent of the total energy content of the nutritional composition or for example 8.0-8.3 percent of the total energy content of the nutritional composition
- a fat content which is at least 49 percent or more of the total energy content of the nutritional composition or especially 50 percent or more for example 52-53 energy % fat, for example 52.5% of the energy of the formula is derived from fat.
- a medium chain fatty acid comprising 8 to 10 carbons content which is 0.5-3 wt % of total amount of fatty acids or for example 1-3% or for example 1-2% of total amount fatty acids in the composition.
- sialic acid content of 18 mg/100 ml or higher, or between 18-25 mg/100 ml.
- a sphingomyelin content of 9-15 mg/100 ml or more than 10 mg/100 ml or especially 13 mg/100 ml.
- a cholesterol content of between 5-10 mg/100 ml or between 7-10 mg/100 ml or for example 0.2-0.3 weight % of cholesterol expressed as percentage of total fat content of the formula or for example 8 mg/100 ml, which is 0.23 wt % cholesterol expressed as percentage of total fat content of the formula.
- whey protein/milk protein concentrate solids rich in phospholipids containing 5-7 weight % of the total dry weight of the composition.

In another embodiment the nutritional composition used according to the invention further comprises
- lipid bound sialic acid as gangliosides of between 1.5-5 wt % of total sialic acid content, or for example 4 wt % lipid bound sialic acid of total sialic acid content.

In one embodiment the energy content used in the nutritional composition to be used according to the invention is for example 58-60 kcal/100 ml and 51.8-53.4 energy % fat. The protein content is for example 1.1-1.25 g/100 ml and 7.8-8.2 energy % protein, and a low NPN content, is for example an NPN content between 0.015-0.020 g/100 ml and a high sialic acid content is for example 18-20 mg/100 ml. The level of milk derived cholesterol is for example 7-9 mg/100 ml.

In another embodiment the energy content in the nutritional composition to be used according to the invention is 60 kcal/100 ml and the composition comprises 52.5 energy % fat. The protein content is 1.2 g/100 ml and the composition comprises 8 energy % protein. In another embodiment of the invention the energy content in the nutritional composition according to the invention is 60 kcal/100 ml and 52.5 energy % fat, the protein content is for example 1.2/000 ml and the composition comprises 8 energy % protein, with non-protein-nitrogen (NPN) content of 0.015-0.020 g/100 ml or for example 0.016 g/100 ml and 13 mg/100 ml of sphingomyelin and a high sialic acid content is for example 19 g/100 ml. The level of milk derived cholesterol is for example 8 mg/100 ml and the composition comprises a medium chain fatty acid (comprising 8 to 10 carbons) content which is less than 3 wt % of total amount of fatty acids.

A nutritional composition to be used according to the invention, may also refer to the composition of the invention as a powder suitable for making a liquid composition after reconstitution with water.

The nutritional composition to be used according to the invention may be prepared from powder by mixing 114 g of a nutritional composition powder with 900 ml water to make 1000 ml of liquid composition according to the invention.

The nutritional composition to be used according to the invention further comprises the following features in any combination;

In other embodiments to be used according to the invention the formula comprises 5-6 wt % whey protein concentrate solids rich in phospholipids and 12-15 wt % cream solids expressed as percentage of the total weight of the solids in the composition.

In one embodiment to be used according to the invention the formula further comprises a sphingomyelin content in the formula of for example between 9-15 mg/100 ml, or to mg/100 ml or higher for example 13 mg/100 ml.

Further embodiments are also alternative embodiments to be used according to the invention.

A nutritional composition to be used according to the present invention wherein the composition comprises intact or partly hydrolysed milk protein.

A nutritional composition to be used according to the present invention wherein the amino acid content in the composition is originated from sources selected from for example; sweet whey solids, casein solids, milk solids and cream solids.

A nutritional composition to be used according to the present invention wherein the sphingomyelin content in the composition according to the invention is between 9-15 mg/too ml, or 10 mg/100 ml or higher, especially 13 mg/100 ml.

A nutritional composition to be used according to the present invention wherein the composition is comprised from the following raw materials;
- sweet whey solids 32-40 kg/1000 kg dry powder composition or between 32.6-39.9 kg/1000 kg dry powder composition
- sodium caseinate between 4.6-5.7 kg/1000 kg dry powder composition or between 4.66-5.69 kg/1000 kg dry powder composition
- skim milk solids between 66-81 kg/1000 kg dry powder composition or between 66.3-81 kg/1000 kg dry powder composition
- whey protein concentrate solids rich in phospholipids between 47-58 kg/1000 kg dry powder composition or between 47.1-57.6 kg/1000 kg dry powder composition
- cream solids between 117-143 kg/1000 kg dry powder composition.

A nutritional composition to be used according to the present invention wherein the composition comprises; sweet whey solids of 36.3 kg/1000 kg dry powder composition, sodium caseinate of 5.18 kg/moo kg dry powder composition, skim milk solids of 73.7 kg/woo kg dry powder composition, whey protein concentrate solids of 52.4 kg/1000 kg dry powder composition, cream solids of 130 kg/moo kg dry powder composition.

A nutritional composition to be used according to the present invention wherein the values described above defining the ingredients in the composition in kg/1000 kg powder is the same when defining the ingredients in the composition by kg/8770 L of ready to drink nutritional composition.

Further the composition may comprise vitamins (see for example vitamins mentioned in Formula EF below), minerals (see for example minerals mentioned in Formula EF below), fats (see for example fats mentioned in Formula EF below or in the detailed description), lactose and/or other essential nutrients (for example choline, taurine, inositol, carnitine, fructo oligo saccharides (FOS), galacto oligo saccharides (GOS), probiotics or nucleotides).

Further, the nutritional composition used according to the invention may comprise smaller amounts of other ingredients, for example less than 7 wt % of the total formula weight. Examples of such other ingredients are other milk solids (not in specified formula) e.g. acid whey protein concentrate, butter milk solids, whole milk solids etc. Said other ingredients may be present as long as the specification of the nutritional composition, described above of the invention is fulfilled.

A nutritional composition to be used according to the present invention wherein the composition comprises; sweet whey solids of 36.3 kg/1000 kg dry powder composition, sodium caseinate of 5.18 kg/1000 kg dry powder composition, skim milk solids of 73.7 kg/1000 kg dry powder composition, whey protein concentrate solids rich in phospholipids of 52.4 kg/1000 kg dry powder composition, cream solids of 130 kg/1000 kg dry powder composition. Further the composition may comprise vitamins (see for example vitamins mentioned in Formula EF below), minerals (see for example minerals mentioned in Formula EF below), fats (see for example fats mentioned in Formula EF below), lactose and/or other essential nutrients (for example choline, taurine, inositol, carnitine).

Further, the nutritional composition to be used according to the invention may comprise other ingredients as long as the specification of the nutritional composition, described above of the invention is fulfilled.

BRIEF DESCRIPTION OF THE DRAWINGS

FIG. 1 outlines the design of a comparative study including infants receiving the experimental formula (EF) or the control formula (SF), as well as breast-fed infants (Reference).

METHODS

Inclusion

From March 2008 to February 2012, 160 formula-fed infants (80 girls and 80 boys) and a breastfed reference (BFR) group with 80 infants (40 girls and 40 boys), all born at Umeå University Hospital, Umeå, Sweden, were recruited after inviting parents by telephone. Inclusion criteria were <2 months of age, gestational age at birth 37-42 weeks, birth weight 2500-4500 grams, absence of chronic illness, and exclusively formula-feeding or, for the breast-fed reference (BFR) group, exclusively breastfeeding at inclusion and mother's intention to exclusively breastfeed until 6 months. All groups were given a recommendation of only small amounts (taste portions) complementary foods between 4 and 6 months.

Randomization and Blinding

Formula-fed infants were stratified for sex and randomized in a computerized model with blocks of 8 to receive EF or SF from inclusion until 6 months of age. Twins were co-randomized to the same intervention group. The intervention was blinded both to parents and staff until all infants had finished the intervention. The intervention was blinded to parents until all infants had completed follow-up. Formula powder was distributed to families together with preparation instructions in identical boxes marked with a code number.

Study Formula

BabySemp® was used as SF and the EF was modified from this. Four weight percent of the protein in the EF came from supplementation with a bovine MFGM-enriched whey protein concentrate (Lacprodan® MFGM-10, Arla Foods Ingredients, Denmark). Macronutrient composition of the EF and SF are presented in Table 1.

TABLE 1

Macronutrient contents in the experimental formula (EF) and standard formula (SF) per 100 ml.

| | EF | SF |
| --- | --- | --- |
| Energy (kcal) | 60 | 66 |
| Proteins (g) | 1.20 | 1.27 |
| Casein (g) | 0.35 | 0.50 |
| Whey (g) | 0.85 | 0.80 |
| Carbohydrates/lactose (g) | 6.0 | 7.4 |
| Lipids (g) | 3.5 | 3.5 |
| Saturated FA (g) | 1.35 | 1.30 |
| Monounsaturated fatty acids (g) | 1.35 | 1.40 |
| Polyunsaturated fatty acids (g) | 0.60 | 0.60 |
| Linoleic acid (mg) | 460 | 460 |
| α-linolenic acid (mg) | 70 | 70 |
| Arachidonic acid (mg) | 15 | 15 |
| Docosahexaenoic acid (mg) | 9 | 9 |
| Cholesterol (mg) | 8 | 4 |
| Phospholipids (mg) | 70 | 30 |

Measurements

Visits were made at inclusion (<2 months), 4 months, 6 months and 12 months. At each visit, anthropometric data, blood and fecal samples were obtained. Parents were asked to complete a symptom diary every day during the intervention period (until 6 months of age) with stool consistency and frequency, any disease symptoms, medication or hospitalization. Stool consistency on every portion was reported as a score from 1 (watery diarrhea) to 4 (hard stools). Between 6-12 months, parents were asked to write down any disease symptom, medication or hospitalization in the diary. Diaries were collected at every visit. All collected symptom diaries were included in the analysis.

Statistical Analyses

Statistical calculations were made using IBM SPSS Statistics Version 19 (©IBM 1989, 2010). All analyses were made on an intention-to-treat basis. Days with disease symptoms and antibiotics use were compared with the non-parametric Mann-Whitney U test. Comparisons of proportions were made by Chi-Square test or, if any cell had an expected count<5, Fisher's Exact Test (2-sided).

Results

Rates of drop-outs and non-compliance are shown in FIG. 1. From inclusion until 6 months of age, symptom diaries recorded by parents were collected from 75 (94%), 74 (93%) and 74 (93%) of the infants covering 89%, 89% and 90% of the total number of study days for the EF, SF and BFR group, respectively. Between 6 and 12 months of age, symptom diaries were collected from 57 (75%), 58 (81%) and 64 (89%) of the infants in the EF, SF and BFR group, respectively.

Number of infants included in the study, included in the analysis (white boxes) and following the intervention/still breast-feeding at 6 months (grey boxes) for the experimental formula (EF), standard formula (SF) and breast-fed reference (BFR) groups.

Infections

During the intervention, from inclusion until 6 months of age, parents of infants fed the EF reported fewer episodes of acute otitis media (AOM) treated with antibiotics compared to parents of infants fed the SF. There were no other significant differences between the formula groups in bacterial infections treated with antibiotics or viral infections leading to hospitalization before 6 months of age, nor between 6 and 12 months of age (Table 2).

TABLE 2

Bacterial infections treated with antibiotics and viral infections leading to hospitalization during the first 12 months of life for the experimental formula (EF), the standard formula (SF) and breast-fed reference (BFR) groups, number (%) of infants.

|  | EF | SF | p-value (EF vs SF) | BFR |
|---|---|---|---|---|
| Inclusion - 6 months | | | | |
| Otitis | 1 (1) | 7 (9) | 0.034 | 0 (0) |
| Pneumonia | 0 (0) | 1 (1) | 1.0 | 0 (0) |
| Other invasive bacterial infection | 1 (1)[a] | 0 (0) | 1.0 | 0 (0) |
| Other non-invasive bacterial infection | 0 (0) | 0 (0) | 1.0 | 5 (7)[b] |
| Gastroenteritis, hospitalized | 0 (0) | 2 (3) | 0.25 | 0 (0) |
| Other viral infection, hospitalized | 1 (1)[c] | 1 (1)[c] | 1.0 | 1 (1)[c] |
| 6-12 months | | | | |
| Otitis | 6 (11) | 4 (7) | 0.53 | 4 (6) |
| Pneumonia | 1 (2) | 2 (3) | 1.0 | 2 (3) |
| Other invasive bacterial infection | 0 (0) | 0 (0) | 1.0 | 0 (0) |
| Other non-invasive bacterial infection | 2 (4)[d] | 2 (4)[e] | 1.0 | 2 (3)[f] |
| Gastroenteritis, hospitalized | 1 (2) | 2 (3) | 1.0 | 0 (0) |
| Other viral infection, hospitalized | 0 (0) | 3 (5)[g] | 0.24 | 1 (2)[h] |

[a]Urinary tract infection
[b]Conjunctivitis (n = 4), skin infection (n = 1)
[c]Obstructive bronchitis
[d]Conjunctivitis (n = 1), skin infection (n = 1)
[e]Skin infection (n = 2)
[f]Skin infection (n = 1), fungal stomatitis (n = 1)
[g]Obstructive bronchitis (n = 1), viral infection not otherwise specified (n = 1), febrile seizure (n = 1)
[h]Obstructive bronchitis The EF group reported less antipyretics use during intervention compared to the SF group (Table 3). 61 (81%), 59 (80%) and 63 (85%) of the infants had received pneumococcal vaccine from 3 months of age in the EF, SF and BFR group, respectively.

TABLE 3

Consumed infection-related medication for the experimental formula (EF), the standard formula (SF) and breast-fed reference (BFR) groups (number (%) of infants and total number of days).

| | EF | | SF | | p-value (EF vs SF) | | BFR | |
|---|---|---|---|---|---|---|---|---|
| | n (%) | Days | n (%) | Days | Proportion | No of days | n (%) | Days |
| Inclusion - 6 months | | | | | | | | |
| Antibiotics | 2 (3) | 18 | 7 (9) | 42 | 0.086 | 0.092 | 5 (7) | 58 |
| Antipyretics | 19 (25) | 54 | 32 (43) | 118 | 0.021 | 0.016 | 33 (45) | 119 |
| Airway dilating | 13 (17) | 63 | 14 (19) | 77 | 0.80 | 0.79 | 15 (20) | 142 |
| 6 months - 12 months | | | | | | | | |
| Antibiotics | 8 (14) | 61 | 8 (14) | 101 | 0.97 | 0.87 | 8 (13) | 77 |
| Antipyretics | 28 (49) | 137 | 30 (52) | 148 | 0.78 | 0.77 | 38 (59) | 226 |
| Airway dilating | 15 (26) | 316 | 18 (31) | 150 | 0.58 | 0.57 | 30 (47) | 278 |

In conclusion, the present study has shown that supplementation with a bovine MFGM fraction to infant formula decreases the incidence of acute otitis media (AOM) in formula-fed infants between 0-6 months of age to a level similar to breast-fed infants. The effect is probably due to antimicrobial and/or immuno stimulating factors of MFGM previously not present in infant formula or present in a lower concentration than in human milk.

Further the production method of the invention is described according to the following embodiments;

A method for producing a nutritional composition for use according to the present invention in order to get a high sialic acid content, a high sphingomyelin content and a high cholesterol content in combination with low protein and energy content, comprising the steps;

providing ingredients per 1000 kg dry powder or per 8770 L ready to drink nutritional composition;
  sweet whey solids between 32-40 kg/1000 kg dry powder composition or per 8770 L ready to drink nutritional composition
  sodium caseinate between 4.6-5.7 kg/1000 kg dry powder composition or per 8770 L ready to drink nutritional composition
  skim milk solids between 66-81 kg/1000 kg dry powder composition or per 8770 L ready to drink nutritional composition
  whey protein concentrate solids rich in phospholipids between 47-58 kg/1000 kg dry powder composition or per 8770 L ready to drink nutritional composition
  cream solids between 117-143 kg/1000 kg dry powder composition or per 8770 L ready to drink nutritional composition
  Further additionally comprising for example vitamins, minerals, fats, lactose and other essential nutrients (for example choline, taurine, inositol, carnitine); and,
  mixing the ingredients.

A method for producing a nutritional composition for use according to the invention wherein no free amino acids are added other than naturally occurring free amino acids present in milk raw materials.

It is further possible to add small amounts of other ingredients into the composition for use according to the invention as long as the specification of the nutritional composition, described above of the invention is fulfilled. For example, acid whey solids can be used.

A method for producing a nutritional composition for use according to the invention wherein no free amino acids are added other than the additions made by adding raw materials from sources selected from; sweet whey solids, casein solids, milk solids and cream solids.

DETAILED DESCRIPTION

Definition of an infant is a child under the age of 12 months.

The use of dairy cream as an ingredient in the present nutritional composition (or the use of dairy cream solids when making a nutritional composition powder to be mixed with water) contributes to the high levels of milk derived cholesterol in the nutritional composition according to the invention. This dairy cream usage contributes to the high levels of cholesterol (5-10 mg/100 ml) in the composition according to the invention. Due to the special composition according to the invention the addition of cholesterol as an ingredient (due to addition of dairy cream and whey protein concentrate rich in phospholipids) gives a similar blood cholesterol level as in breastfed infants during the feeding period but probably also later in life for those infants fed with the nutritional composition according to the invention.

The cream also improves the taste of the invention formula. The formula also contains whey protein concentrate rich in phospholipids which also contribute to the content of milk derived cholesterol in the invention formula as well as of the milk derived phospholipid sphingomyelin. Sphingomyelin is included in an amount of preferably 10 mg/100 ml or higher. The invention formula comprises for example on dry basis between 26-32 weight percent fat or for example on dry basis 3.7 weight percent fat whereof between 15-19 weight percent of the total amount fat is vegetable fat, or for example 18.5 weight percent of total fat content is vegetable fat.

The content of medium chain fatty acids (MCT) comprising 8 to 10 carbons in the nutritional composition according to the invention is for example 0.5-3 weight percent of total amount of fatty acids or for example 1-2 weight percent of total amount fatty acids in the composition. The invention formula mimics the content of MCT in breast milk. Mature breast milk has 1-2 weight percent MCT of total fatty acids (R. A. Gibson et al. *Am. J. Clin. Nutr.* 34: 252-257, 1981).

Further sweet whey, cream and whey protein concentrate rich in phospholipids, all comprise cGMP. By, for example not removing cGMP from the nutritional composition according to the invention the sialic acid content is kept high. High sialic acid content is for example about 10-25 mg/100 ml or between 18-20 mg/100 ml of the nutritional composition according to the invention. By not removing cGMP from the raw materials used to produce the formula, the nutritional composition according to the invention is likely to for example increase the level of sialic acid in saliva (more similar to breastfed). The higher intake of sialic acid can have an effect on for example morbidity and cognitive behavior in the invention formula-fed infants.

Sphingomyelin is the major component of the phospholipid fraction in breast milk, and is found in lower concentrations in conventional nutritional compositions compared to the formula according to the invention. Sphingomyelin is metabolized to ceramide which concentration correlates with degree of myelination of the nervous system. Experiments on rats with experimentally inhibited myelination have shown that supplements of sphingomyelin increases myelination (K. Oshida et al. *Pediatr Res,* 2003, vol. 53 (4) 589-593). The milk derived sphingomyelin content in the formula according to the invention is 9 mg/100 ml or higher, or between 9-15 mg/100 ml, or 13 mg/100 ml.

The nutritional composition according to the invention comprises a special composition of raw materials. The nutritional composition according to the present invention still has a low burden-effect on the metabolic system of the formula-fed infant although it comprises cGMP.

The levels of arachidonic acid (ARA) and docosahexaenoic acid (DHA) in the nutritional composition according to the invention are of similar levels as present in breast milk. (Brenna et al *DHA and ARA concentrations in human breast milk worldwide* Am J Clin Nutr 85, p 1457-1464).

The present invention provides a nutritional composition and a method for producing such a composition.

Non-Protein-Nitrogen

Non-protein nitrogen (NPN) is a term used to refer collectively to components which are not proteins which are present in food and which comprise nitrogen. (NPN in milk is mainly urea-nitrogen (about 50%), creatine, creatinine, NH3 etc.)

Since it is important not to have a surplus of nitrogen in formulas for infants we have endeavoured to have a low level of NPN<20 mg/100 ml in the nutritional composition according to the invention, for example a low non-protein nitrogen (NPN) value between 0.015-0.020 g/100 ml. Surprisingly the invention formula has a low NPN value although it has a totally new composition of raw materials.

Amino Acid Profile

It is known that an infant formula needs a predetermined amino acid profile to fulfill the children's need. This is also regulated by the government Commission Directive 2006/141/EC. The amino acid supply in an infant's first months of life must be sufficient in quantity as well as quality to fulfill the needs of this period of life. Guidelines, recommendations with minimum values have been established with regard to amino acid composition of infant formulas. An amino acid profile of the nutritional composition according to the invention is presented in the table below. The clinical study confirms that the amino acid composition in the invention formula is adequate for the requirement for growth.

| Amino acid | Minimum value Commission Directive (mg/100 kcal) | Interval according to the invention (mg/100 kcal) |
| --- | --- | --- |
| Leucine | 166 | 197-229 or 217 |
| Lysine | 113 | 165-192 or 180 |
| Methionine | 23 | 36-42 or 40 |
| Cystine | 38 | 40-46 or 44 |
| Phenylalanine | 83 | 83-96 or 87 |
| Tyrosine | 76 | 64-74 or 72 |
| Threonine | 77 | 114-132 or 124 |
| Tryptophan | 32 | 35-41 or 39 |
| Valine | 88 | 116-135 or 127 |
| Isoleucine | 90 | 116-135 or 127 |
| Histidine | 40 | 46-53 or 50 |
| Cystine + Methionine* | 61 | 76-88 or 84 |
| Phenylalanine + Tyrosine* | 159 | 147-170 or 159 |

The concentration of methionine and cysteine can be calculated together since the amino acid cysteine can be formed from methionine. Further, the concentration of tyrosine and phenylalanine can be calculated together since the amino acid tyrosine can be formed from phenylalanine. Therefore also combined levels of these amino acids are specified in the table above*.

Amino Acid Sources of the Present Nutritional Composition:

The formula according to the invention has a composition which is such that the wanted amino acid profile is achieved without addition of any free amino acid. The formula according to the invention is manufactured without addition of any free amino acid (or isolated amino acids) to get a desired amino acid profile.

The wording free amino acids or isolated amino acids in this application mean descriptions for an amino acid substance which is isolated as a free acid or as a salt.

The formula according to the present invention is therefore not enriched with isolated amino acids, for example free amino acids. This is an advantage since free amino acids are usually bitter in taste. It is also expensive to add amino acids in their pure form. By using the ingredients according to the present invention the nutritional composition according to the invention does not need further addition of free or isolated amino acids and is therefore more similar to breast milk in taste.

Production Method

The formula according to the invention is according to one embodiment produced by mixing the below ingredients in kg per 1000 kg nutritional composition dry powder or kg per 8770 L finished nutritional composition.

| Raw material | Interval in the formula according to the invention (kg/1000 kg dry powder or kg/8770 L) | Amount in the formula according to the invention (kg/1000 kg dry powder or kg/8770 L) |
| --- | --- | --- |
| Sweet whey solids | 32-40 | 36 ± 2 |
| Sodium caseinate | 4.6-5.7 | 5.2 ± 0.3 |
| Skimmed milk solids | 66-81 | 74 ± 4 |
| Whey protein concentrate solids (rich in phospholipids) | 47-58 | 52 ± 3 |
| Cream solids | 117-143 | 130 ± 6 |

The nutritional composition may further comprise vitamins, minerals, fats, lactose and/or other essential nutrients (for example choline, taurine, inositol, carnitine, nucleotides).

Further, the nutritional composition according to the invention may comprise other ingredients as long as the specification of the nutritional composition, described above of the invention is fulfilled.

Sweet Whey

Sweet whey is rich in α-lactalbumin. The high α-lactalbumin content makes it ideally suited as a protein source in infant formulas in order to fulfil desired amino acid pattern. Sweet whey also contains cGMP which is a source of sialic acid.

Cream

Cream is a natural and valuable source of short and medium chain fatty acids as well as milk derived cholesterol. The milk derived phospholipids in cream are besides important nutritional substances also valuable emulsifiers. The formula according to the invention may be manufactured using cream or cream solids. The fat content of the cream used according to the invention is for example of 36-40 wt % fat or especially 37 wt % fat.

Caseinate Sodium caseinate or partly other salts of caseinates may be used in the invention formula.

Hydrolysed Protein

The protein source in the formula to be used according to the invention may be a hydrolysed protein.

Below is an exemplified description of the production process of the formula to be used according to the invention, the following example of the invention is not limiting the scope of the invention:

The present invention provides a ready to drink nutritional composition or a powder formula intended to be reconstituted with water to a ready to drink nutritional composition and a method for producing such compositions.

In one embodiment the composition is a powder suitable for making a liquid composition after reconstitution with water. Alternatively the composition is for example a ready to use liquid product.

Below is an example of ingredients for making the nutritional composition to be used according to the invention.

Example of amounts of ingredients (kg/1000 kg) of a dry powder formula to be used according to the invention which is intended to be reconstituted with water before usage (amounts of ingredients for the a ready to drink formula is below described in kg/8770 L);

| Description | Amount (interval) (kg/1000 kg or kg/8770 L)) |
|---|---|
| Lactose | 476-527 |
| Cream solids | 123-136 |
| Skim milk solids | 70.0-77.3 |
| Rape seed oil | 51.6-57.0 |
| Palm olein oil | 51.6-57.0 |
| Whey protein concentrate solids rich in phospholipids | 49.7-55.0 |
| Sun flower oil | 38.3-42.3 |
| Sweet whey solids | 34.5-38.1 |
| Sun flower oil HO | 24.9-27.6 |
| Minerals | 16.1-17.8 |
| Sodium caseinate | 4.92-5.44 |
| Dry lecithin | 4.26-4.70 |
| Arachidonic acid oil | 1.60-3.50 |
| Docosahexaenoic acid oil | 1.60-2.17 |
| Vitamin mix | 1.29-1.43 |
| Choline, taurine, myo-inositol, L-carnitine | 1.21-1.34 |

Examples of Production Methods According to the Invention, not Limiting the Scope of the Invention;

Production Method of a Powder Nutritional Composition According to the Invention:

Milk based raw materials are mixed to a slurry. Standardized milk or milk powder and liquid whey or whey powder are mixed, if necessary, with additional water. Suitable equipment mixes the slurry in a tank with negative pressure to reduce foaming and incorporation of air.

Emulsifier and fat soluble vitamins are added to a blend of vegetable oils. The fat phase is then incorporated in the milk phase either in the mixing tank or dosed in line before homogenization. In line dosing of oil means that a part of the milk phase is heated, oil is dosed into the stream, homogenized and cooled down again.

Water soluble vitamins, additives such as taurine and minerals with a pro oxidative effect such as ferrous- and copper salts are added just before concentrating the slurry by means of a finisher to a final dry matter content of 50-55%. The concentrate is then heat treated to ensure the microbiological quality, spray dried, the powder cooled and stored. After quality control, product is packed or, if it is a semi product, first blended, combining the spray dried semi product with additional minerals, vitamins, bioactive ingredients and citric acid.

Production Method of a Ready-to-Drink Nutritional Composition According to the Invention:

Water, made alkaline with calcium hydroxide, is mixed with whey or whey powder. The solution is neutralized before adding the carbohydrate source and standardized milk. Additional ingredients such as choline, taurine, inositol and carnitine are added before pasteurisation and fat phase injection and homogenization. The fat phase is made up of vegetable oils, emulsifiers and fat soluble vitamins. Before sterilization, vitamins are added and quality check is performed. The product is UHT-treated, a quick heat treatment at about 140° C. for 5 seconds, cooled and aseptically packed.

(UHT means Ultra High Temperature. Products from an UHT-process have good keeping qualities with retained nutritional values).

Below is an example of the nutritional composition according to the invention and also a description of a control formula, both used in a comparative study. The below example of the invention is not limiting to the scope of the invention;

The infant formula (Formula EF) used in the study is an example of a nutritional composition according to the invention. The Control Formula (SF) is used for comparison. The comparative Control Formula (SF) is a representative infant formula of good quality available on the market. Compare also the specification of the formulas in Table 1 above The formulas included in the study have the following compositions (see table below)—Formula EF is an example of the nutritional composition according to the invention;

| Description | Formula EF (kg/1000 kg) | Control Formula (SF) (kg/1000 kg) |
|---|---|---|
| Lactose | 502 | 536 |
| Cream solids | 130 | 89.6 |
| Skim milk solids | 73.7 | 105 |
| Rape seed oil | 54.3 | 43.4 |
| Palm olein oil | 54.3 | 75.9 |
| Whey protein concentrate solids (rich in phospholipids) | 52.4 | |
| Sun flower oil | 40.3 | 30.7 |
| Sweet whey solids | 36.3 | 61.1 |
| Sun flower oil HO | 26.3 | 30.7 |
| Minerals | 17.0 | 10.1 |
| Sodium caseinate | 5.18 | 6.56 |
| Dry lecithin | 4.48 | 4.03 |
| Arachidonic acid oil | 3.33 | 2.91 |
| Docosahexaenoic acid oil | 2.07 | 1.80 |
| Vitamin mix | 1.38 | 1.48 |
| Choline, taurine, myo-inositol, L-carnitine | 1.27 | 1.04 |
| L-arginine | | 0.689 |
| Potassium citrate | 4.68 | 2.58 |
| Calcium carbonate | 3.33 | 3.33 |
| Potassium chloride | 3.08 | 2.19 |
| Calcium hydrogenphosphate | 1.94 | |
| Magnesium sulphate | 1.78 | 0.583 |
| Sodium chloride | 1.40 | 0.972 |
| Ascorbic acid | 1.08 | 1.22 |
| Choline chloride | 0.648 | 0.486 |
| Sodium citrate | 0.500 | |
| Taurine | 0.415 | 0.370 |
| Ferrous sulphate | 0.178 | 0.150 |
| myo-Inositol | 0.135 | 0.120 |
| Zinc sulphate | 0.0863 | 0.0769 |
| Ascorbyl palmitate | 0.0782 | 0.0751 |
| L-carnitine | 0.0756 | 0.0656 |
| Vitamin D3 | 0.0539 | 0.0480 |
| Vitamin A | 0.0476 | 0.0424 |
| DL-a-tocopherol | 0.0350 | 0.0362 |
| Calcium D-pantothenate | 0.0296 | 0.0263 |
| Niacin | 0.0180 | 0.0160 |
| Copper sulphate | 0.00846 | 0.00754 |
| Thiamine hydrochloride | 0.00676 | 0.00602 |
| Vitamin K1 | 0.00561 | 0.00500 |
| Pyridoxine hydrochloride | 0.00546 | 0.00486 |
| Potassium iodide | 0.00073 | 0.00073 |
| Folic acid | 0.00062 | 0.00055 |
| Sodium selenite | 0.00039 | 0.00039 |
| Biotin | 0.00011 | 0.00010 |

Formula EF, which is a nutritional composition to be used according to the invention, with the ingredients described above, comprises the nutritional values presented below as ready for consumption (114 g of powder formula EF is mixed with 900 ml water which gives 1000 ml ready to drink product);

a total energy content of 60 kcal/100 ml, a protein content of 1.2 g/100 ml, an energy content from protein of 8.0 (E %) of the total energy content of the nutritional composition a protein:energy ratio of 2.0/100 kcal a fat content which is 52.5 (E %) of the total energy content of the nutritional composition according to Formula EF a medium chain fatty acid (comprising 8 to 10 carbons) content of 1.6 wt % of total amount of fatty acids in Formula EF sialic acid content of 19 mg/100 ml a cholesterol content of 8 mg/100 ml lipid bound sialic acid as gangliosides of 4 wt % of total sialic acid content sphingomyelin content of 13 mg/100 ml Formula EF has a high content of sialic acid from natural sources compared to standard formulas. The sialic acid content comes from two different sources, one, from whey protein concentrate solids (rich in phospholipids), which is lipid bound and the other from GMP, which is bound to carbohydrates. Formula EF has a high milk derived content of sphingomyelin from natural sources compared to the Control Formula (SF), namely whey protein concentrate solids (rich in phospholipids). It is an advantage to use said natural sources of sialic acid and sphingomyelin.

Energy % (E %) is a normal way to express the amount of kcal, which comes from fat, protein and carbohydrates in a nutritional formulation. The National food agency in Sweden (Livsmedelsverket) has identified this on http.//www.slv.se/sv/grupp1/Mat-och naring/naringsrekommendationer/Kalorier-kilojoule-och energiprocent---hur raknar-man/

The control formula, with the ingredients described in the table above, comprises the nutritional values presented below as ready for consumption (130 g of powder control formula is mixed with 900 ml water gives 1000 ml ready to drink product);

a total energy content of 66 kcal/100 ml a protein content of 1.27 g/100 ml, a protein energy % content of 7.7 of the total energy content of the nutritional composition according to the control formula a fat energy % content of 44.7 of the total energy content of the nutritional composition according to the control formula a medium chain fatty acid (comprising 8 to 10 carbons) content of 1.5 wt % of total amount of fatty acids in the control formula sialic acid content of 16 mg/100 ml a cholesterol content of 4 mg/100 ml lipid bound sialic acid as gangliosides of 2 wt % of total sialic acid content according to the control formula sphingomyelin 1.8 mg Study Study Design The study is a randomized double-blind intervention trial with exclusively breastfed infants as a reference group which means that three groups of children participate in the study:

1) Children who are breastfed.

2) Children who receive experimental infant formula, (EF), according to the invention (see description above).

3) Children who receive a representative infant formula of good quality, herein called "Control Formula" (SF) (see description above).

The study was set up to detect a possible difference of 0.5 standard deviation (SD) for each outcome variable, which corresponds to a weight difference of about 0.4 kg at 6 months or a difference of 3.25 percent of body fat measured by plethysmography at 2 months of age. The visual acuity equivalent to 0.5 SD is 0.25 octaves at 4 months of age, which is the difference seen when compared to children with feeding with or without DHA supplement. With a statistical "power" of 80% a group size of just over 60 children is required. 80 children were recruited per group, which gave a sufficient number of children per group completing the study. FIG. 1.

DISCUSSION

The hypothesis, that MFGM supplementation to infant formula would give a reduction in infectious morbidity, was supported by the findings that infants fed the EF had a lower incidence of AOM and a reduced number of days with antipyretic medication during the intervention period. Observational studies have shown a clear protective effect of breast-feeding on some infections (Ip, S., et al., *A summary of the Agency for Healthcare Research and Quality's evidence report on breastfeeding in developed countries*. Breastfeed Med, 2009. 4 Suppl 1: p. S17-30), and several studies with supplementation of different factors to infant formula have been performed in order to try to narrow this gap. Lactoferrin supplementation to infant formula was associated with fewer lower respiratory tract infections during the first year of life (King, J. C., Jr., et al., *A double-blind, placebo-controlled, pilot study of bovine lactoferrin supplementation in bottle-fed infants*. J Pediatr Gastroenterol Nutr, 2007. 44(2): p. 245-514).

Several components of MFGM have been described to have an antimicrobial effect. In a proteomic characterization of human MFGM, 191 proteins were identified of which 19.9% were involved in immune function (Liao, Y., et al., *Proteomic characterization of human milk fat globule membrane proteins during a 12 month lactation period*. J Proteome Res, 2011. 10(8): p. 3530-41.6). In bovine MFGM, 120 different proteins were identified of which 4% had immunological effects and 21% had unknown effect (Liao, Y., et al., *Proteomic characterization of human milk fat globule membrane proteins during a 12 month lactation period*. J Proteome Res, 2011. 10(8): p. 3530-41). Analysis of MFGM-enriched commercial milk fractions have shown high concentration of relevant MFGM proteins in both whey protein concentrates and butter milk concentrates (Affolter, M., et al., *Qualitative and quantitative profiling of the bovine milk fat globule membrane proteome*. J Proteomics, 201. 73(6): p. 1079-88). Further, the lipid fraction of bovine MFGM had antiviral effect in vitro (Fuller, K. L., et al., *Milk fat globule membrane isolated from buttermilk or whey cream and their lipid components inhibit infectivity of rotavirus in vitro*. J Dairy Sci, 2013. 96(6): p. 3488-97), and gangliosides of the MFGM have been suggested to play an important role in the development of intestinal microbiota, the gut immunity and consequently in the defense of infections (Rueda, R., *The role of dietary gangliosides on immunity and the prevention of infection*. Br J Nutr, 2007. 98 Suppl 1: p. S68-73).

Supplementation with MFGM has previously been shown to have positive effect on infections in older children. MFGM enrichment to complementary food to 6-12 months old infants, showed positive effects on diarrhea in a study in Peru (Zavaleta, N., et al., *Efficacy of an MFGM-enriched complementary food in diarrhea, anemia, and micronutrient status in infants*. J Pediatr Gastroenterol Nutr, 2011. 53(5): p. 561-8) and MFGM-enriched formula milk to children aged 2.5-6 years gave a reduction of febrile episodes in a Belgian study (Veereman-Wauters, G., et al., *Milk fat glob-* ule membrane (INPULSE) enriched formula milk decreases febrile episodes and may improve behavioral regulation in young children. Nutrition, 2012. 28(7-8): p. 749-52).

The mechanism behind the effect on AOM seen in the present study is unclear. One possible explanation could be that factors of MFGM are essential building stones in the cellular or humoral immune system and contribute to its maturation. Growing evidence also suggests a link between the gut microbiota and the peripheral immune system (Cerf-Bensussan, N. and V. Gaboriau-Routhiau, *The immune system and the gut microbiota: friends or foes*? Nat Rev Immunol, 2010. 10(10): p. 735-44), and dietary antimicrobial and immuno-stimulating factors from the MFGM could, by affecting the gut microbiota, have positive effect on the infants' defense against pathogens. Anyhow, our interpretation is that the EF has had a general effect on the immune function rather than a specific effect on AOM, supported by the findings that the use of antipyretics was larger in the SF group and that several other outcomes showed a trend towards favour to the EF group, for example hospitalization due to gastroenteritis until 12 months of age and breathing and coughing until 6 months of age. See Table 4.

ventilation bottles creates a negative pressure continuing to the middle ear and probably increasing the risk of AOM (Brown, C. E. and B. Magnuson, *On the physics of the infant feeding bottle and middle ear sequela: ear disease in infants can be associated with bottle feeding*. Int J Pediatr Otorhinolaryngol, 2000. 54(1): p. 13-20). Unfortunately, we have no data on bottle manufacturer in our study population, but with the randomization, we do not expect any difference between the EF and SF group.

The EF group had slightly harder stools than the SF group, but their parents did not report more gastrointestinal symptoms or use of laxatives. The stools of the BFR group was looser than in the formula groups and the BFR group had less gastrointestinal symptoms and less use of laxatives, well in line with previous studies (Tunc, V. T., et al., *Factors associated with defecation patterns in 0-24-month-old children*. Eur J Pediatr, 2008. 167(12): p. 1357-62).

In conclusion, the present study has shown that supplementation with a bovine MFGM fraction to infant formula decreases the incidence of AOM in formula-fed infants between 0-6 months of age to a level similar to breast-fed infants. The effect is probably due to antimicrobial and/or

TABLE 4

Reported infection-related symptoms for the experimental formula (EF), the standard formula (SF) and breast-fed reference (BFR) groups (number (%) of parents reporting each symptom and total number of days).

| | EF | | SF | | p-value (EF vs SF) | | BFR | |
|---|---|---|---|---|---|---|---|---|
| | n (%) | Days | n (%) | Days | Proportion | No of days | n (%) | Days |
| Inclusion - 6 months | | | | | | | | |
| Fever | 37 (49) | 110 | 35 (47) | 192 | 0.80 | 0.78 | 43 (58) | 105 |
| Coughing | 46 (61) | 721 | 53 (72) | 615 | 0.18 | 0.29 | 49 (66) | 572 |
| Breathing difficulties | 10 (13) | 30 | 14 (19) | 61 | 0.35 | 0.36 | 12 (16) | 42 |
| Skin rash | 13 (17) | 77 | 19 (26) | 292 | 0.22 | 0.23 | 22 (30) | 480 |
| 6 months - 12 months | | | | | | | | |
| Fever | 43 (75) | 230 | 39 (67) | 129 | 0.33 | 0.16 | 51 (80) | 339 |
| Coughing | 44 (77) | 638 | 45 (78) | 949 | 0.96 | 0.79 | 57 (89) | 1204 |
| Breathing difficulties | 10 (18) | 26 | 12 (21) | 55 | 0.81 | 0.57 | 11 (18) | 48 |
| Skin rash | 13 (23) | 181 | 8 (14) | 256 | 0.21 | 0.29 | 24 (38) | 597 |

The incidence of infectious diseases during the first 6 months in developed countries is low, and AOM is the most common cause of antibiotic treatment (McCaig, L. F., R. E. Besser, and J. M. Hughes, *Trends in antimicrobial prescribing rates for children and adolescents*. JAMA, 2002. 287 (23): p. 3096-102). Antibiotics are most useful in children under two years of age with bilateral AOM or with both AOM and otorrhea (Venekamp, R. P., et al., *Antibiotics for acute otitis media in children*. CochraneDatabase Syst Rev, 2013. 1: p. CD000219). In the present study, all infants that were diagnosed with AOM received antibiotic treatment. The introduction of pneumococcal vaccination to infants, has changed the epidemiology of otitis in infants in many countries (Coker, T. R., et al., *Diagnosis, microbial epidemiology, and antibiotic treatment of acute otitis media in children: a systematic review*. JAMA, 2010. 304(19): p. 2161-9), and about 80% of the infants in the present study received 10-valent pneumococcal vaccine from 3 months of age after the introduction of general pneumococcal vaccination for infants born in the Umeå area after October 2008.

The ventilation of the bottle used can also influence the risk of otitis media in bottle-fed infants, under- or nonimmune stimulating factors of MFGM previously not present in infant formula or present in a lower concentration than in human milk. The results should be of interest for future recommendations on the composition of infant formulas.

The invention claimed is:

1. A method for the treatment or prevention of otitis, comprising administering to an infant in need of such treatment or prevention an effective amount of a nutritional composition,
   wherein the nutritional composition is a ready-to-use product or a ready-to-use product reconstituted with water from a manufactured powder, comprising whey or milk protein concentrate solids rich in phospholipids and milk fat globule membrane (MFGM),
   wherein the whey or milk protein concentrate solids rich in phospholipids and MFGM further comprises one or more bioactive compounds selected from the group consisting of lactoferrin, α-lactalbumin, butyrophilin, MUC1, PAS6/7, gangliosides, CD14, TLR1 and TLR4, IgG, cGMP, sialic acid, and phospholipids, and
   wherein said whey or milk protein concentrate solids rich in phospholipids and MFGM comprises at least 20 wt % phospholipids based on total lipid of the enriched phospholipid whey or milk protein concentrate solid source.

2. The method according to claim 1, wherein the nutritional composition comprises:
   a total energy content which is 67 kcal/100 ml or lower,
   a protein content which is 1.5 g/100 ml or lower,
   an energy content from protein which is 7.2-8.6 percent of the total energy content of the nutritional composition,
   an energy content from fat which is at least 47 percent or more of the total energy content of the nutritional composition,
   a medium chain fatty acid content comprising 8 to 10 carbons which is less than 3 weight % of total amount of fatty acids,
   a sialic acid content which is 10 mg/100 ml or higher,
   a cholesterol content which is 4-10 mg/100 ml,
   a sphingomyelin content which is 7-15 mg/100 ml, and
   wherein the whey or milk protein concentrate solids rich in phospholipids and MFGM comprises 5-7 weight % of the total dry weight of said nutritional composition.

3. The method according to claim 2, wherein:
   the energy content from protein is 7.2-8.4 percent of the total energy content of the nutritional composition,
   the energy content from fat is at least 49 percent of the total energy content of the nutritional composition,
   the cholesterol content in the nutritional composition is 5-10 mg/100 ml, and
   the sphingomyelin content in the nutritional composition is 9-15 mg/100 ml.

4. The method according to claim 2, wherein the cholesterol content is 0.2-0.3 weight % of the total fat content of the nutritional composition.

5. The method according to claim 2, wherein the cholesterol content in the nutritional composition is between 7-10 mg/100 ml.

6. The method according to claim 2, wherein said cholesterol is milk derived cholesterol.

7. The method according to claim 2, wherein the energy content from fat is between 47-54% of the total energy content of the nutritional composition.

8. The method according to claim 2, wherein the energy content in the nutritional composition is lower than 60 kcal/100 ml.

9. The method according to claim 2, wherein the sialic acid content in the nutritional composition is between 10-30 mg/100 ml.

10. The method according to claim 1, wherein the nutritional composition further comprises lipid bound sialic acid as gangliosides, wherein the content of lipid bound sialic acid as gangliosides is 1.5-5 weight % of the total sialic acid content.

11. The method according to claim 1, wherein the nutritional composition further comprises intact or partly hydrolysed milk protein.

12. The method according to claim 1, wherein amino acid content in the nutritional composition derives from milk solids, sweet whey solids, casein solids, and cream solids.

13. The method according to claim 1, wherein the energy content from protein is 8-9% of the total energy content of the nutritional composition.

14. The method according to claim 1, wherein the nutritional composition further comprises sphingomyelin between 9-17 mg/100 ml.

15. The method according to claim 1, wherein the otitis is bacterial otitis.

16. The method according to claim 15, wherein the bacterial otitis is Acute Otitis Media (AOM).

17. The method according to claim 1, wherein the nutritional composition is given to infants up to 6 months of age.

* * * * *